United States Patent [19]

Kappas et al.

[11] Patent Number: 4,997,828

[45] Date of Patent: Mar. 5, 1991

[54] METHOD OF WEIGHT CONTROL BY LOW LEVEL ADMINISTRATION OF COBALT PROTOPORPHYRIN OR COBALT MESOPORPHYRIN

[75] Inventors: Attallah Kappas; Richard A. Galbraith, both of New York, N.Y.

[73] Assignee: The Rockefeller University, New York, N.Y.

[21] Appl. No.: 310,854

[22] Filed: Feb. 14, 1989

[51] Int. Cl.[5] .................... A61K 31/40; A61K 31/555
[52] U.S. Cl. .................................... 514/184; 514/185; 514/410
[58] Field of Search .................. 514/184, 185, 410; 540/145

[56] References Cited

U.S. PATENT DOCUMENTS

| | | | |
|---|---|---|---|
| 4,393,071 | 7/1983 | Fujii et al. | 514/410 |
| 4,656,186 | 4/1987 | Bommer et al. | 540/145 |
| 4,657,902 | 4/1987 | Kappas et al. | 514/185 |
| 4,693,885 | 9/1987 | Bommer et al. | 540/145 |
| 4,782,049 | 11/1988 | Kappas et al. | 514/185 |

FOREIGN PATENT DOCUMENTS

87/04927  8/1987  World Int. Prop. O. .......... 514/410

OTHER PUBLICATIONS

Sato et al, Juzen Igakukai 67, 384-9 (1961), Chemical Abstracts, vol. 61, 1964, Abstract 8792d.
Smith et al, Pharmacology 34:9-16 (1986), Kikuchi et al, Molocular and Coll. Biochim., 3727-41 (1981).
Smith et al, Proc. Natl. Acad. Sci, U.S.A. 79 7537-41, Dec. 1982.
Feuer et al, Xenobiotica, 1985, 15(5), 407-12.
Ibrahim et al, Clinical Res. 27(3), 578A, 1979.
Belovetskaya et al, Fiziol. Biokhim. Ontog. 1983, 80-1, Chemical Abs., vol. 100, 1984, 4577d–Abstract.
Int. J. Biochem. 15(4), 1981.
Foye, Principles of Medicinal Chemistry (Philadelphia, Lea and Fibiger, 1976), pp. 659-661.
Gilbraith et al, Pharmacology, 34(5), 1987, 241-9, Chemical Abstracts, vol. 106, 1987, Abstract 188765n.

Primary Examiner—Mukund J. Shah
Assistant Examiner—E. C. Ward
Attorney, Agent, or Firm—Wyatt, Gerber, Burke and Badie

[57] ABSTRACT

Cobalt protoporphyrin and cobalt mesoporphyrin are administered to animals to achieve weight loss and improved protein to fat ratio without decrease in hormone concentration.

20 Claims, 5 Drawing Sheets

METHOD OF WEIGHT CONTROL BY LOW LEVEL ADMINISTRATION OF COBALT PROTOPORPHYRIN OR COBALT MESOPORPHYRIN

This invention is concerned with methods of controlling the weight of animals, i.e., living beings including mammals such as man; bovines, particularly beef cattle; sheep, goats; poultry, especially chickens, ducks and turkeys; as well as fish, particularly those raised in fish farms such as salmon and trout; and, in general, all animals of economic importance in addition to pets by treatment with cobalt protoporphyrin (CoPP) or cobalt mesoporphyrin (CoMP). Both of these compounds are known. It is also known to treat animals with CoPP or CoMP.

U.S. Pat. No. 4,393,071 relates to methods of treating malignant tumors with porphyrins including mesoporphyrin and protoporphyrin. Neither CoPP or CoMP are specifically named or illustrated. Moreover, if CoPP or CoMP were administered at the levels described for those porphyrins which are specifically named and illustrated there would be a serious question of toxicity.

Drummond and Kappas in Proc. Natl. Acad. Sci. USA 79:2284 (1982) describe the administration of CoPP to animals as a method to deplete the cytochrome P-450 content of the liver. The lowest level of administration described by the coauthors is 25 $\mu$m/kg body weight.

Sako and coworkers have published the results of their studies of administration of CoPP to mice and rats to control the growth of Sarcoma 180 (ascites form), Sarcoma 180 (nodular form), Yoshida sarcoma (nodular form) and Ehrlich's carcinoma (ascites form). See Juzen Igakukai Zasshi 67: 384 (1966), 67; 390 (1961) and 67: 395 (1961).

Kappas and Drummond in copending and commonly assigned patent application Ser. No. 07/310,899, filed Feb. 14, 1989, describe parenteral administration of isotonic compositions containing CoPP and/or CoMP to animals to achieve reduced activity of the endocrine system, weight control and improved (P/F) ratio. More specifically, they describe the administration of the active compounds to limit the production of gonadal hormones and to suppress the production of thyroid hormones. This patent application also describes the administration of CoPP and CoMP to animals, including humans, to achieve weight control and to improve the P/F ratio. At the levels of administration described in the application endocrine suppression, weight control and improved P/F ratio all take place simultaneously.

The invention defined in the copending patent application is extremely valuable for all of the reasons described therein. However, in many instances it would be useful, in fact highly desirable, to control weight and P/F ratio without endocrine involvement. For example, the use of the active agents to control the weight of individuals in their reproductive years might be contraindicated because of the concurrent limited production of gonadal hormones.

It has now been discovered that the endocrine suppression activity of CoPP and CoMP declines as the dosage is decreased so that at a dosage of about 10 $\mu$m/kg b.w. (body weight), say 9.8 $\mu$m/kg b.w. it becomes negligible and at 4 $\mu$m/kg b.w. it has effectively disappeared. However, the weight control activity and the improved P/F ratio continues even down to as low as 0.1 $\mu$m/kg b.w. It is, therefore, possible to control the weight and P/F ratio of animals by treatment of animals in need of such control or improved P/F ratio with from about 0.1 $\mu$m/kg b.w. to about 4 $\mu$m/kg b.w. The preferred range is 0.1 to 0.3 $\mu$m/kg b.w. because at this low dosage there is substantially no endocrine suppression activity.

FIG. 1 graphically illustrates the results observed in Example 1. Taken together with the results reported in Table I, it shows a decrease in body weight without decrease in hormone concentration on administration of CoPP to adult male rats.

FIG. 2 graphically illustrates the results observed in Example 2. Taken in conjunction with the results reported in Table II, it shows a decrease in body weight with no decrease in testosterone levels on administration of CoPP to adult male dogs.

Figure 1:
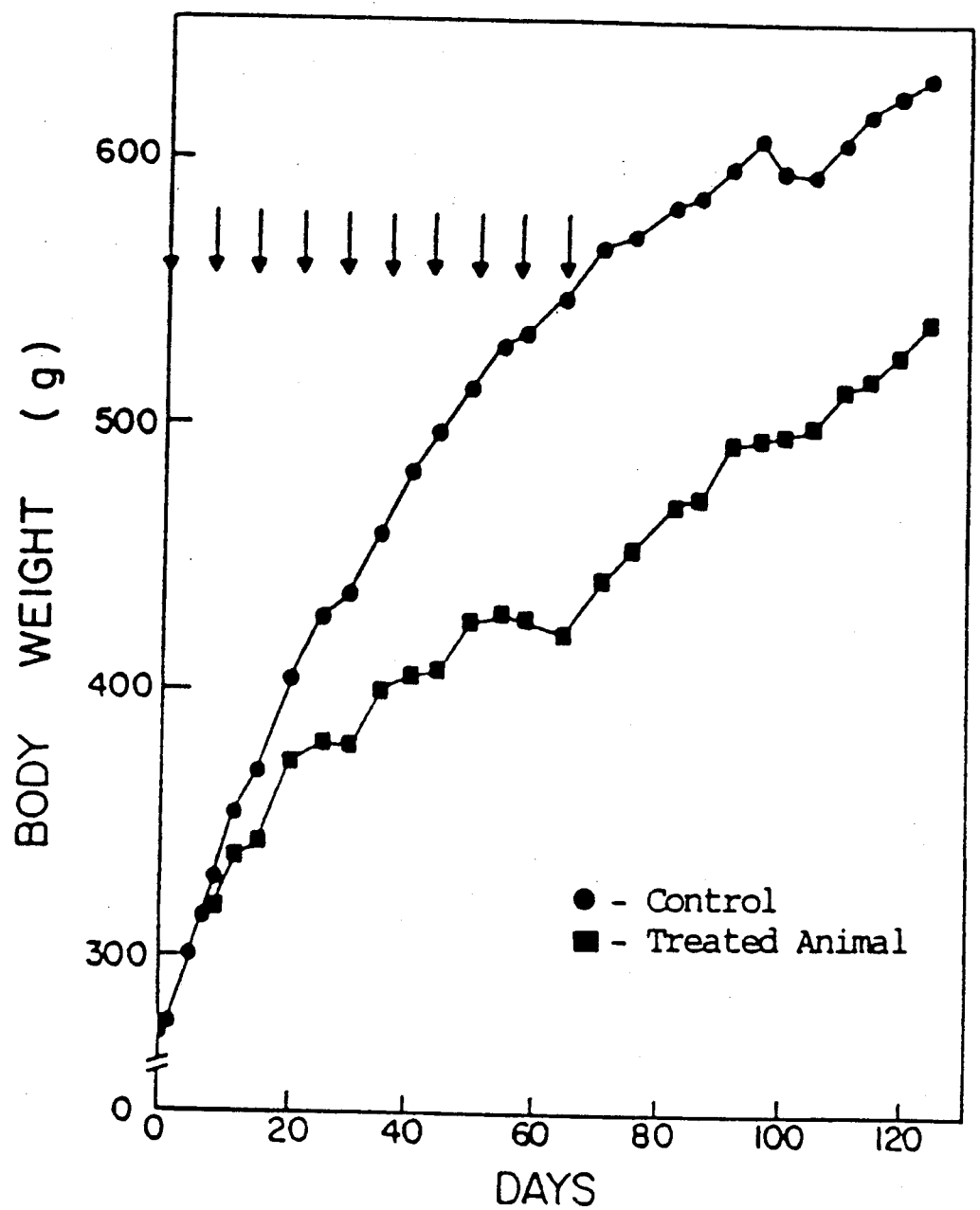

Comparable results to those illustrated in the figures for CoPP are obtained with CoMP. Similar administration of either CoPP or CoMP results in improved P/F ratios.

The CoPP and CoMP utilized in this invention appear to achieve their desired effect of weight control by two mechanisms. One is appetite suppression. The other is actual weight loss by a metabolic mechanism which is not fully understood at this time.

The methods of the invention are especially useful for the treatment of diabetes mellitus, Type II, the so called adult type. This type of diabetes is normally treated by diet control. For this utility, the two pronged attack of appetite suppression coupled with actual weight loss is ideal.

The compounds of the invention will normally be administered parenterally, i.e. intravenously, subcutaneously or intramuscularly in sterile, isotonic parenteral solutions. For such solutions, any of a wide variety of pharmaceutically acceptable carriers currently in use for the preparation of parenteral solutions may be employed. The solutions may be buffered, for example with a phosphate buffer to a pH of about 7 to 8, preferably 7.4 to 7.5, and contain such solutes as saline or glucose. The solutions may also contain a polyhydroxy alcohol such as ethylene or propylene glycol. The active compounds may also be administered in solution or suspension in a sterile inert oil such as sesame or safflower oil. A typical dosage regimen for humans will be from about 0.5 to 2 $\mu$m/kg b.w. per week.

Typically, isotonic solutions for use in this invention can be prepared by dissolving the selected amount of CoPP or CoMP in 0.1 M aqueous sodium hydroxide solution, adjusting to the selected pH with 1 M hydrochloric acid, and making up to volume with 0.9 aqueous sodium chloride solution. For the low levels of active agent utilized in the practice of this invention, parenteral compositions will normally be prepared to contain from about 1 to 15 mg/ml.

The physician or veterinarian will determine the specific dosage, and it will depend upon such well understood factors as the age, weight and general health of the patient. Typically, treatment will be initiated at a dosage level of about 0.5 to 1 μm/kg b.w. and the patient will be observed so that the decline in weight is not too precipitous. Too rapid a decline in weight could elicit toxic effects similar to those observed in starvation, i.e., kidney damage, ketosis, electrolyte imbalance, etc. Therefore, the object will be to decrease weigh gradually, in effect to titrate the patient so that the weight is brought under control without attendant undesirable effects.

The active compounds of the invention may also be administered intraventricularly. For most patients this method of administration is neither necessary nor practical. It does have the advantage that desired weight control can be achieved at dosage levels at the low end of the dosage range utilized for parenteral administration. A typical range for intraventricular administration is from about 0.1 to 0.5 μm/kg body weight. Additionally the rate of weight loss is much higher than with parenteral administration. The procedure is useful with bedridden individuals and with the morbidly obese.

The following examples are given by way of illustration only and should not be understood as limitations of this invention since many apparent variations are possible without departing from its spirit or scope. In the examples, the vehicle is isotonic aqueous saline at a pH of about 7.4.

EXAMPLE 1

Adult male Sprague-Dawley rats (≈250 g) were injected subcutaneously with CoPP 1 μmol/kg b.w. (12 rats) or vehicle (12 rats) on day 0. Thereafter, injections (Vertical arrows in FIG. 1) were repeated weekly until 10 doses had been given. Animals were allowed Purina rat chow and water ad libitum and animal weights were recorded thrice weekly; means are presented in FIG. 1 ( ● is control and ■ treated animals). On day 71, 6 control rats and 6 CoPP-treated rats were sacrificed, blood collected for hormone determinations and hepatic mitochondrial and microsomal fractions prepared for biochemical assays. These procedures were repeated at day 124 for the remainder of the animals. The results are listed in Table 1. Although differences in weights of control and CoPP-treated rats were highly significant, there were no significant differences in naso-anal length, hormone concentrations or heme pathway and cytochrome P-450-dependent enzyme activities.

EXAMPLE 2

Figure 2:
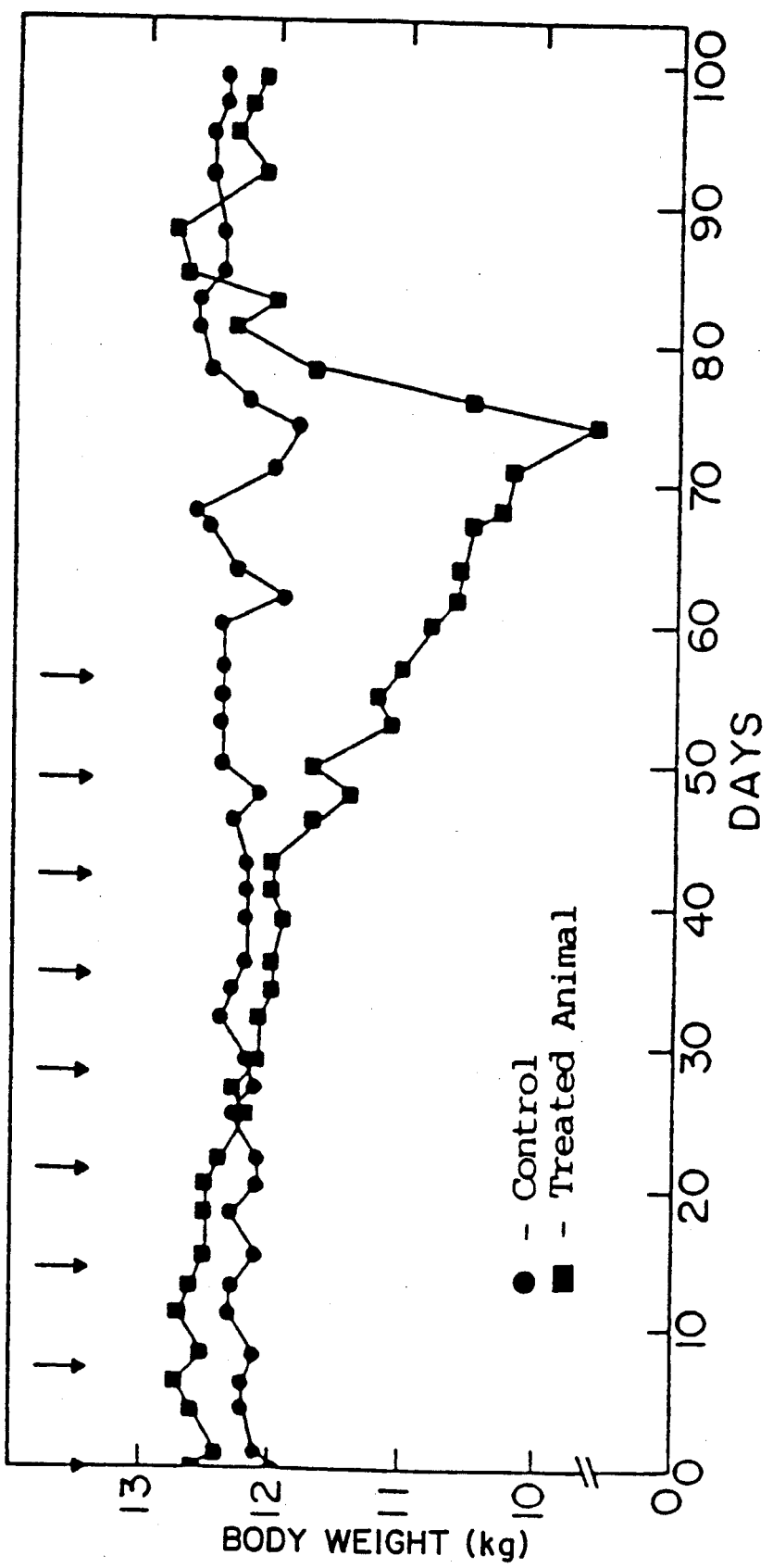

Adult male Beagle dogs (≈1 year) were housed in single runs with free access to Purina dog chow and water. On day 0, 3 animals were injected intramuscularly in the upper posterolateral aspect of the hindlimb with CoPP 2.5 μmol/kg b.w., and 3 animals with control vehicle. Injections (Vertical arrows in FIG. 2) were repeated weekly, in alternating hindlimbs, until a total of 9 doses had been given. Animal weights were recorded thrice weekly and means are presented in FIG. 2 ( ● is control and ■ is treated animals). Mean weights were unchanged during the first 3 weeks of treatment, but progressively decreased thereafter to a nadir at day 74, when CoPP-treated dogs had lost approximately 25% of their body weight. By day 84, animals had returned to their pre-treatment weights. Blood was collected for testosterone determinations before the start of the experiment and on days 62 and 112; as can be seen in Table II, there was no effect of CoPP on testosterone concentrations.

EXAMPLE 3

Figure 3:
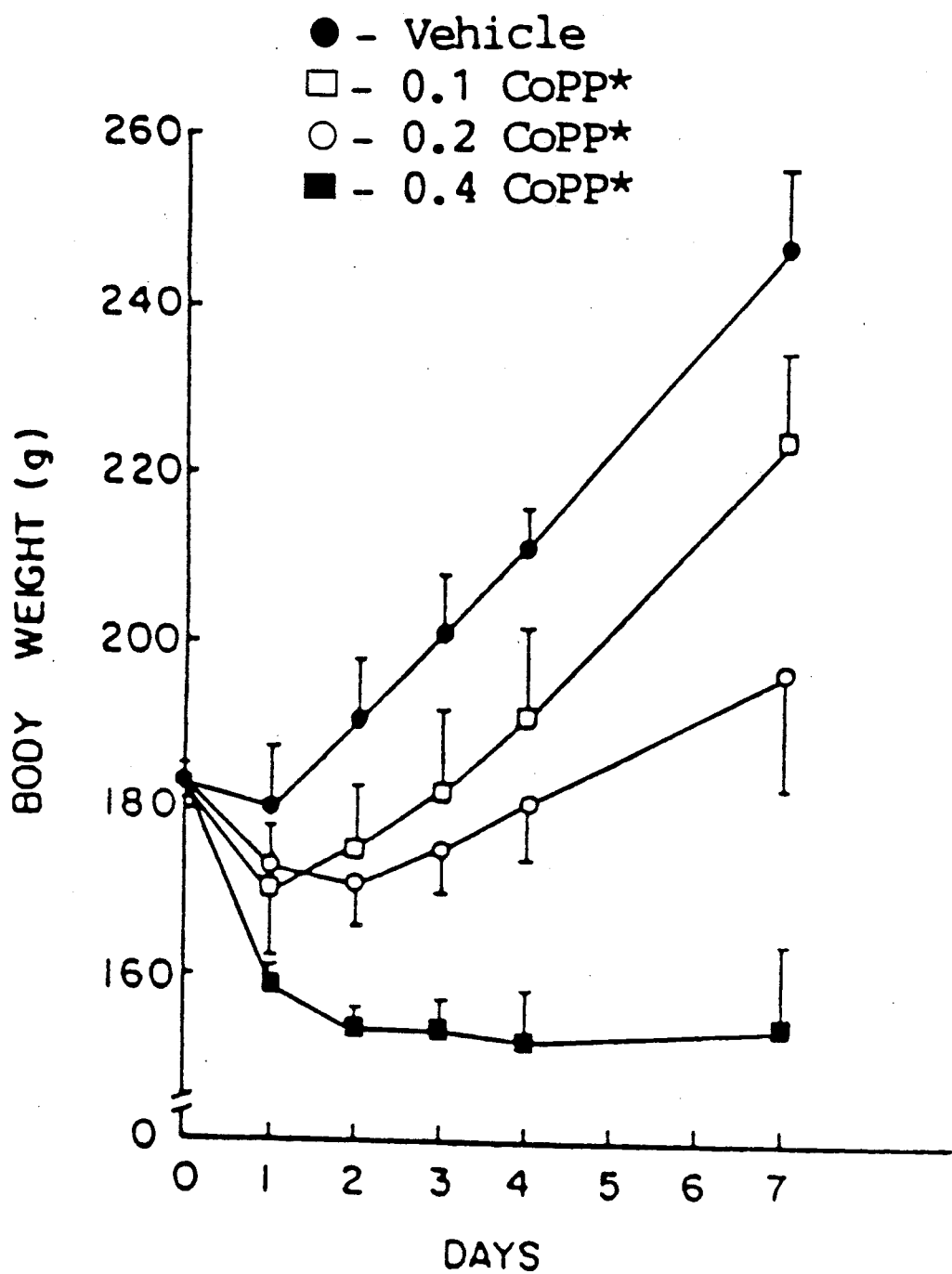
FIG. 3 shows weight loss achieved in adult male rats on intraventricular administration of CoPP as described in Example 3.

Adult male rats were anesthetized during stereotaxic placement of chronic indwelling catheters into the third ventricle of the brain. After 3–4 days post-operative recovery, animals were injected intraventricularly (i/vt) with small volumes (<10μl) of vehicle (●) or CoPP 0.1 (■), 0.2 (o) or 0.4 (■) μmol/kg b.w. Daily weights were recorded and the means±SEM of 4–6 animals per group are displayed in FIG. 3. The effects of I/vt CoPP were dose responsive but i/vt dosages were approximately 50–100 fold less than those required to elicit the same changes by s/c administration.

EXAMPLE 4

Figure 4A:
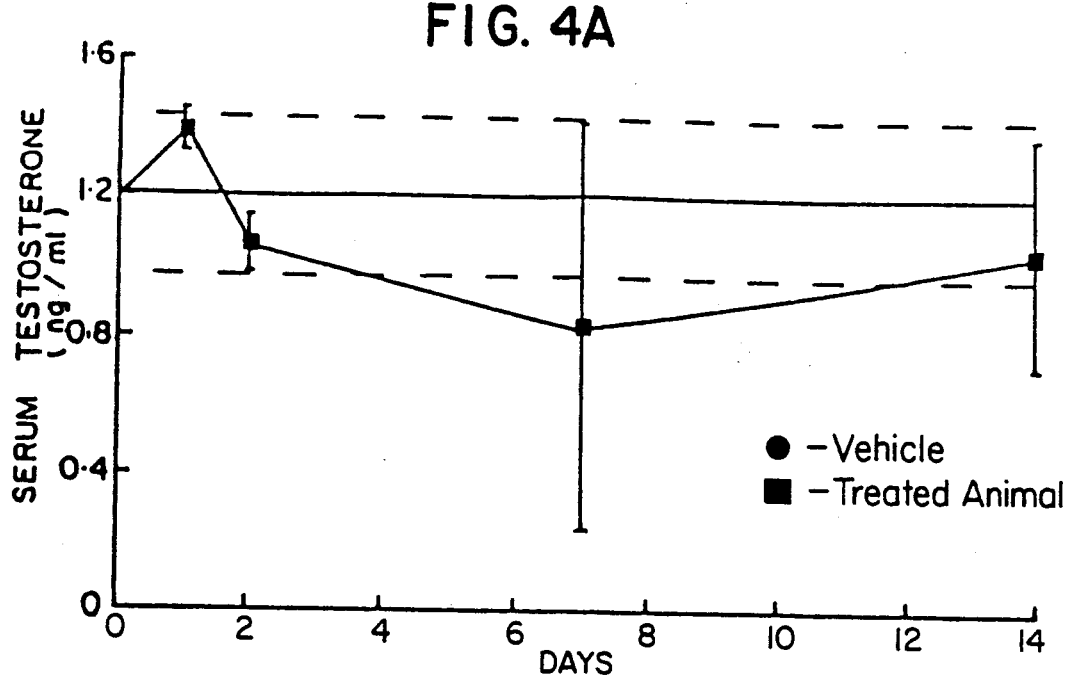
FIG. 4 shows the results reported in Example 4. The example describes the intraventricular administration of CoPP to adult male rats to achieve weight loss without significant changes in testosterone concentration.
Figure 4B:
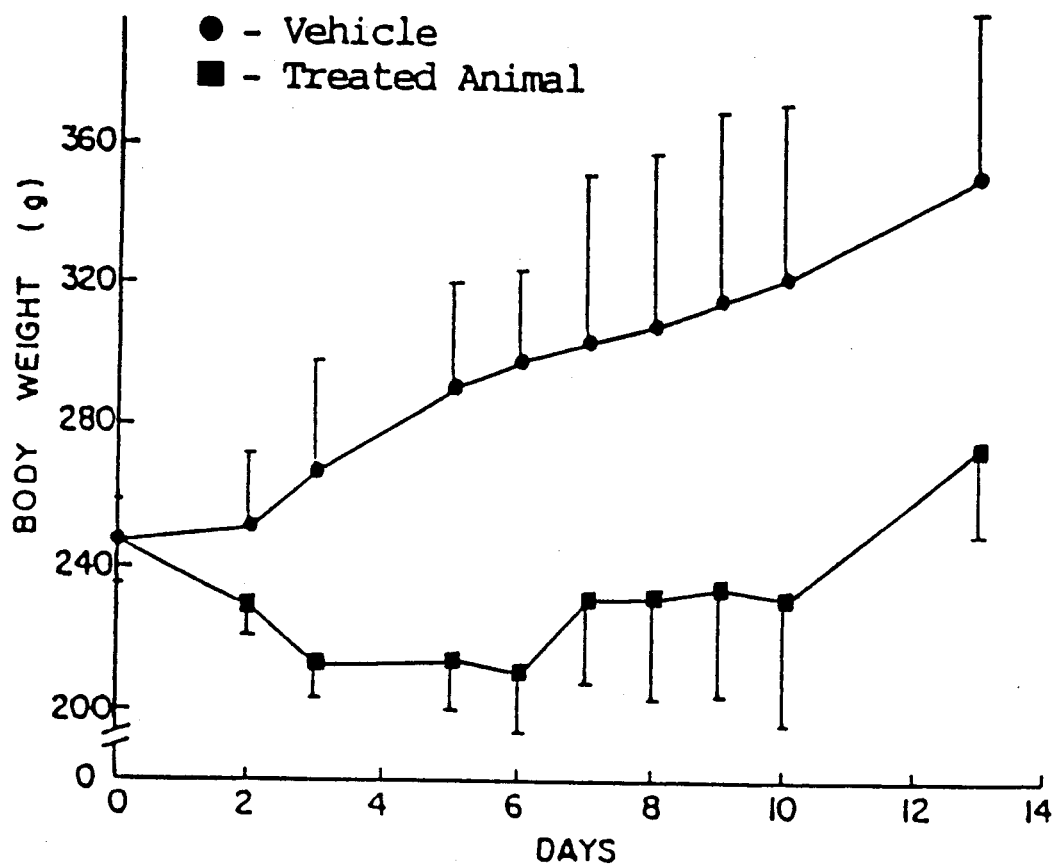

FIG. 4 depicts the means ±SEM of the body weights of 5 adult male rats treated i/vt with vehicle (●) and 5 animals with CoPP 0.4 μmol/kg b.w. (■, lower panel). Although CoPP-treated animals displayed typical weight loss, testosterone concentrations of CoPP-treated rats were not significantly different from vehicle-treated rats (means±SEM indicated, respectively, by solid and broken lines).

EXAMPLE 5

Figure 5:
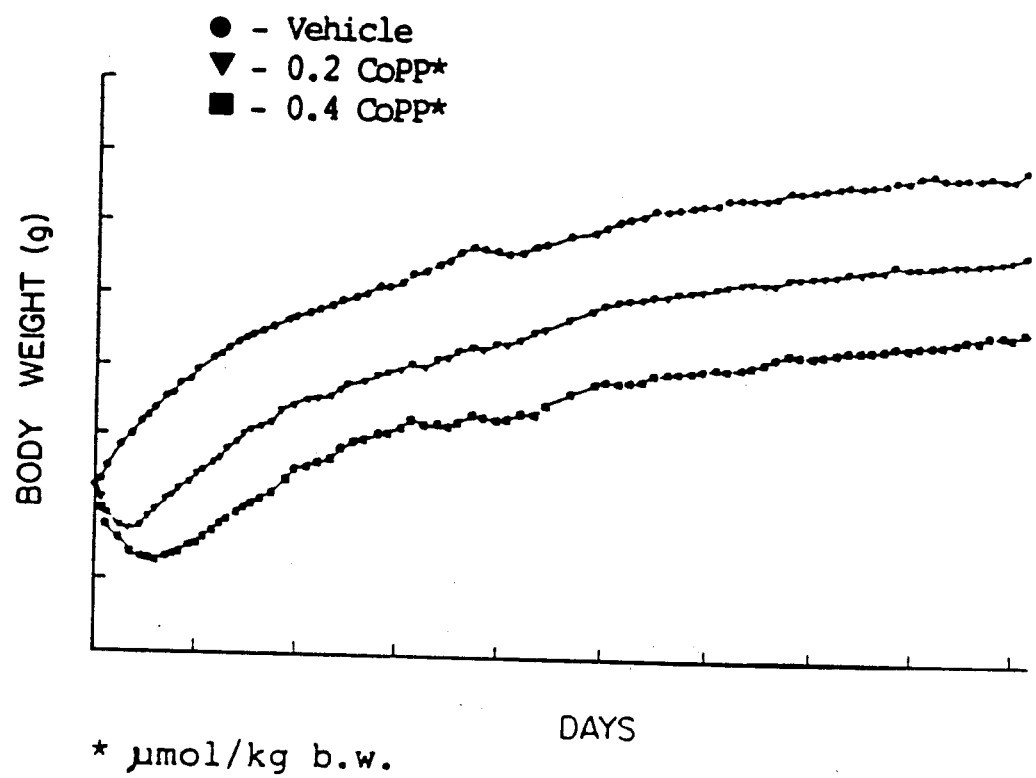
FIG. 5 illustrates the results reported in Example 5 and shows prolonged weight loss following a single intraventricular administration of CoPP.

The prolonged loss of body weight following single i/vt treatments with CoPP 0.2 (▼) or 0.4 (■) μmol/kg b.w. are contrasted with that of vehicle-treated rats (●) in FIG. 5 (n=4). It will be seen that treatment with a low level of active compound resulted in a prompt decrease in weight. The differential between treated and untreated animals was maintained for the duration of the treatment.

TABLE I

The effects of 10 serial doses of CoPP 1 μmol/kg b.w. on weight, hormone concentrations and heme pathway and cytochrome P-450-dependent activities.

|  | Control | CoPP-treated | t** |
|---|---|---|---|
| Day 71 |  |  |  |
| Body weight* (g) | 568 ± 16 | 442 ± 5 | 7.54 |
| Naso-anal length (cm) | 26.6 ± 0.33 | 25.8 ± 0.11 | 2.18 |
| Testosterone (ng/ml) | 1.96 ± 0.29 | 1.72 ± 0.23 | 0.66 |
| Cytochrome P-450 (nmol/mg protein) | 1.06 ± 0.23 | 0.70 ± 0.12 | 1.37 |
| Heme oxygenase (nmol bilirubin/mg prot/hr) | 1.85 ± 0.15 | 2.08 ± 0.21 | 0.91 |
| δ-Aminolevulinic acid synthase (μmol ALA/mg prot/90') | 0.29 ± 0.02 | 0.30 ± 0.01 | 0.71 |
| Aryl hydrocarbon hydroxylase (pmol 8OHBP/mg prot/hr) | 275 ± 24 | 291 ± 28 | 0.44 |
| 7-Ethoxycoumarin de-ethylase (μmol/mg prot/hr) | 0.41 ± 0.04 | 0.53 ± 0.03 | 4.74 |
| Ethylmorphine demethylase (μmol form/mg prot/hr) | 0.43 ± 0.05 | 0.49 ± 0.04 | 0.96 |
| Aniline hydroxylase (nmol p-aminop./mg prot/hr) | 59 ± 3.48 | 74 ± 4.62 | 2.68 |
| DAY 124 |  |  |  |
| Body Weight (g) | 633 ± 39 | 541 ± 12 | 2.24 |
| Naso-anal length (cm) | 27 ± 0.22 | 27 ± 0.11 | 0.67 |
| Testosterone (ng/ml) | 2.64 ± 0.25 | 3.59 ± 0.90 | 1.02 |
| LH (ng/ml) | 21.1 ± 3.29 | 24.2 ± 6.14 | 0.44 |
| Insulin | 156 ± 47.6 | 191 ± 43.6 | 0.53 |

TABLE I-continued

The effects of 10 serial doses of CoPP 1 μmol/kg b.w. on weight, hormone concentrations and heme pathway and cytochrome P-450-dependent activities.

|  | Control | CoPP-treated | t** |
|---|---|---|---|
| (μU/ml) | | | |

*n = 12; for all other parameters, n = 6 animals per treatment.
**As calculated by Student's T-test. The only significant changes are in weight differences.

TABLE II

The effects of 9 serial doses of CoPP 2.5 μmol/kg b.w. on serum testosterone concentrations in male Beagle dogs.

| | Testosterone (ng/ml) | |
|---|---|---|
| | Control (n = 3) | CoPP-treated (n = 3) |
| Day 0 | 1.82 ± 0.65 | 2.03 ± 0.57 |
| Day 62 | 1.73 ± 0.52 | 2.15 ± 1.52 |
| Day 112 | 1.67 ± 0.03 | 1.92 ± 0.83 |

What is claimed is:

1. A method of controlling weight gain in animals in need of such control without concurrent decrease in endocrine activity which comprises parental administration of from 0.1 to about 4 μm/kg body weight of cobalt mesoporphyrin.

2. A method as in claim 1 wherein the animal is a human.

3. A method as in claim 1 wherein the amount of cobalt mesoporphyrin administered is from 0.1 to 3 μm/kg body weight.

4. A method of controlling the protein to fat ratio in animals in need of such control without concurrent decrease in endocrine activity which comprises parenteral administration of from 0.1 to about 4 μm/kg body weight of cobalt mesoporphyrin.

5. A method as in claim 4 wherein the animal is a human.

6. A method as in claim 4 wherein the amount of cobalt mesoporphyrin administered is from 0.1 to 3 μm/kg body weight.

7. A method of controlling weight gain in animals in need of such control without concurrent decrease in endocrine activity which comprises intraventricular administration of from 0.1 to 0.4 μm/kg body weight of cobalt mesoporphyrin.

8. A method as in claim 7 wherein the animal is a human.

9. A method of controlling the protein to fat ratio weight gain in animals in need of such control without concurrent decrease in endocrine activity which comprises intraventricular administration of from 0.1 to 0.4 μm/kg body weight of cobalt mesoporphyrin.

10. A method as in claim 9 wherein the animal is a human.

11. A method of controlling weight gain in animals in need of such control without concurrent decrease in endocrine activity which comprises parenteral administration of from 0.1 to about 4 μm/kg body weight of cobalt protoporphyrin.

12. A method as in claim 11 wherein the animal is a human.

13. A method as in claim 11 wherein the amount of cobalt protoporphyrin administered is from 0.1 to 3 μm/kg body weight.

14. A method of controlling the protein to fat ratio in animals in need of such control without concurrent decrease in endocrine activity which comprises parenteral administration of from 0.1 to about 4 μm/kg body weight of cobalt protoporphyrin.

15. A method as in claim 14 wherein the animal is a human.

16. A method as in claim 14 wherein the amount of cobalt protoporphyrin administered is from 0.1 to 3 μm/kg body weight.

17. A method of controlling weight gain in animals in need of such control without concurrent decrease in endocrine activity which comprises intraventricular administration of from 0.1 to 0.4 μm/kg body weight of cobalt protoporphyrin.

18. A method as in claim 17 wherein the animal is a human.

19. A method of controlling the protein to rat ratio in animals in need of such control without concurrent decrease in endocrine activity which comprises intraventricular administration of from 0.1 to 0.4 μm/kg body weight of cobalt protoporphyrin.

20. A method as in claim 19 wherein the animal is a human.

* * * * *